US008449870B2

(12) United States Patent
Wang et al.

(10) Patent No.: US 8,449,870 B2
(45) Date of Patent: *May 28, 2013

(54) STABLE COSMETIC EMULSION WITH POLYAMIDE GELLING AGENT

(75) Inventors: Tian Xiang Wang, Dix Hills, NY (US); Hernando Brieva, Manalapan, NJ (US); Dexin Luo, Fresh Meadows, NY (US); Paul Henry Marotta, Farmingdale, NY (US); John Richard Castro, Huntington Station, NY (US); Shahan Nazar, Garden City, NY (US); Carl C. Orr, Scotch Plains, NJ (US); Richard A. Konik, Manorville, NY (US)

(73) Assignee: Color Access, Inc., Melville, NY (US)

( * ) Notice: Subject to any disclaimer, the term of this patent is extended or adjusted under 35 U.S.C. 154(b) by 1250 days.

This patent is subject to a terminal disclaimer.

(21) Appl. No.: 10/481,230

(22) PCT Filed: Jun. 19, 2002

(86) PCT No.: PCT/US02/19548
§ 371 (c)(1),
(2), (4) Date: May 6, 2004

(87) PCT Pub. No.: WO02/102322
PCT Pub. Date: Dec. 27, 2002

(65) Prior Publication Data
US 2004/0202626 A1  Oct. 14, 2004

Related U.S. Application Data

(60) Provisional application No. 60/388,154, filed on Jun. 11, 2002.

(51) Int. Cl.
*A61Q 1/06* (2006.01)
*A61Q 1/10* (2006.01)

(52) U.S. Cl.
USPC .......................... 424/64; 424/70.7; 424/401

(58) Field of Classification Search
None
See application file for complete search history.

(56) References Cited

U.S. PATENT DOCUMENTS

| | | |
|---|---|---|
| 2,379,413 A | 7/1945 | Bradley |
| 2,450,940 A | 10/1948 | Cowan et al |
| 2,662,068 A | 12/1953 | Floyd |
| 2,663,649 A | 12/1953 | Winkler |
| 2,890,097 A | 6/1959 | Coe |
| 2,962,461 A | 11/1960 | Toussaint |
| 3,086,914 A | 4/1963 | Soloway |
| 3,141,787 A | 7/1964 | Goetze |
| 3,148,125 A | 9/1964 | Striause et al |
| 3,156,572 A | 11/1964 | Carlick |
| 3,412,115 A | 11/1968 | Floyd |
| 3,615,289 A | 10/1971 | Felton |
| 3,645,705 A | 2/1972 | Miller |
| 3,778,394 A | 12/1973 | Lovald |
| 3,819,342 A | 6/1974 | Gunderman |
| 3,857,960 A | 12/1974 | Mackles |
| 3,926,655 A | 12/1975 | Miles |
| 3,969,087 A | 7/1976 | Saito |
| 4,051,159 A | 9/1977 | Tsoucalas |
| 4,062,819 A | 12/1977 | Mains |
| RE29,871 E | 12/1978 | Papantoniou |
| 4,128,436 A | 12/1978 | O'Hara |
| 4,137,306 A | 1/1979 | Rubino |
| 4,150,002 A | 4/1979 | Drawert |
| 4,275,054 A | 6/1981 | Sebag et al. |
| 4,278,658 A | 7/1981 | Hooper |
| 4,337,298 A | 6/1982 | Karim |
| 4,341,671 A | 7/1982 | Bolze |
| 4,376,194 A | 3/1983 | Tanaka |
| 4,438,240 A | 3/1984 | Tanaka |
| 4,466,936 A | 8/1984 | Schapel |
| 4,536,405 A | 8/1985 | Nara |
| 4,552,693 A | 11/1985 | Hussain |
| 4,571,267 A | 2/1986 | Drawert |
| 4,655,836 A | 4/1987 | Drawert |
| 4,663,428 A | 5/1987 | Okitu |
| 4,699,779 A | 10/1987 | Palinczar |
| 4,712,571 A | 12/1987 | Remz |
| 4,769,285 A | 9/1988 | Rasmussen |

(Continued)

FOREIGN PATENT DOCUMENTS

| | | |
|---|---|---|
| CA | 1319306 | 6/1993 |
| DE | 4217673 A1 | 12/1993 |

(Continued)

OTHER PUBLICATIONS

Bush Boake allen Technical Servises, pp. 1-8 (Oct. 1998).*
Int'l Search Report, Dec. 18, 2002.
Uniqema; Product Information Bulletin; Monamid S; Surfactant; Mona; Alkanolamides; For Personal Care; Printed Feb. 1993; pp. 1-3.
John A. Wenninger and G.N. McEwen, Jr., Ph.D., J.D.; Editors; International Cosmetic Ingredient Dictionary and Handbook; Monographs; Seventh Edition; 1997; vol. 2; pp. 1340-1342; Published by The Cosmetic, Toiletry, and Fragrance Assoc.; Washington, D.C.
Goldschmidt AG; Goldschmidt Personal Care; Degussa.; Creating Essentials; Tagat® Ch 40; TAGAT® CH 60; Tagat® L2; Tagat® O2V; Tagat® S; Tagat® S 2; Mild nonionic surfactants, solubilizers; pp. 1-5.
Supplementary European Search Report; EP04776319.8; PCT/US2004017934; Completion Date: Mar. 25, 2009; Date of Mailing: Apr. 1, 2009.

(Continued)

*Primary Examiner* — Jyothsna Venkat
(74) *Attorney, Agent, or Firm* — Cynthia R. Miller

(57) ABSTRACT

The present invention relates to a gelled cosmetic emulsion comprising an oil phase, an aqueous phase and a gelling system which contains at least one non-siloxane based polyamide in a sufficient amount to gel the emulsion. The polyamide can have an tertiary amide, ester, acid, or amine terminal end group. The emulsion is stabilized with an alkylene oxide containing emulsion stabilizer. The polyamide resin is stabilized with a resin stabilizer containing an atom with a certain electronegativity. The emulsions of the present invention are substantially transparent and when colorants are added the color is especially bright and clear. The emulsions are used in lipstick and mascara products as well as other gel and stick products.

5 Claims, No Drawings

U.S. PATENT DOCUMENTS

| | | | |
|---|---|---|---|
| 4,820,765 A | 4/1989 | Whyzmuzis | |
| 4,830,774 A | 5/1989 | LaPetina et al. | |
| 4,871,536 A | 10/1989 | Arraudeau | |
| 5,047,167 A | 9/1991 | Steyn et al. | |
| 5,061,481 A | 10/1991 | Suzuki et al. | |
| 5,188,831 A | 2/1993 | Nicoll et al. | |
| 5,219,560 A | 6/1993 | Suzuki et al. | |
| 5,272,241 A | 12/1993 | Lucarelli | |
| 5,324,506 A | 6/1994 | Calvo | |
| 5,342,894 A | 8/1994 | Robeson | |
| 5,362,482 A | 11/1994 | Yoneyama | |
| 5,372,852 A | 12/1994 | Titterington | |
| 5,389,363 A | 2/1995 | Snyder | |
| 5,429,816 A | 7/1995 | Hofrichter | |
| 5,472,686 A | 12/1995 | Tsubaki et al. | |
| 5,500,209 A | 3/1996 | Barr et al. | |
| 5,510,452 A | 4/1996 | Santhanam | |
| 5,534,246 A | 7/1996 | Herb et al. | |
| 5,536,871 A | 7/1996 | Santhanam | |
| 5,540,853 A | 7/1996 | Trinh | |
| 5,603,925 A | 2/1997 | Ross et al. | |
| 5,610,199 A | 3/1997 | Cohen | |
| 5,612,043 A | 3/1997 | Deprez | |
| 5,618,523 A | 4/1997 | Zysman | |
| 5,620,693 A | 4/1997 | Piot | |
| 5,645,632 A | 7/1997 | Pavlin | |
| 5,667,770 A | 9/1997 | Szweda | |
| 5,683,817 A | 11/1997 | Kenmochi | |
| 5,719,255 A | 2/1998 | Heucher et al. | |
| 5,747,625 A | 5/1998 | Furukawa | |
| 5,750,127 A | 5/1998 | Rokitowski | |
| 5,750,489 A | 5/1998 | Garcia | |
| 5,773,595 A | 6/1998 | Weuthen | |
| 5,783,657 A * | 7/1998 | Pavlin et al. | 528/310 |
| 5,807,968 A | 9/1998 | Heinrich et al. | |
| 5,830,483 A | 11/1998 | Seidel | |
| 5,849,275 A | 12/1998 | Calello | |
| 5,849,278 A | 12/1998 | Piot | |
| 5,874,069 A | 2/1999 | Mendolia | |
| 5,882,363 A | 3/1999 | Spaulding | |
| 5,891,424 A | 4/1999 | Bretzler | |
| 5,919,441 A | 7/1999 | Mendolia | |
| 5,922,309 A | 7/1999 | Brewster | |
| 5,965,112 A | 10/1999 | Brieva | |
| 5,972,354 A | 10/1999 | de la Poterie | |
| 5,972,359 A | 10/1999 | Sine | |
| 5,976,514 A | 11/1999 | Guskey | |
| 5,981,680 A | 11/1999 | Petroff | |
| 5,993,832 A * | 11/1999 | Lorant et al. | 424/401 |
| 5,998,570 A | 12/1999 | Pavlin et al. | |
| 6,007,799 A | 12/1999 | Lee | |
| 6,019,962 A | 2/2000 | Rabe | |
| 6,024,944 A | 2/2000 | Hansenne | |
| 6,045,823 A | 4/2000 | Vollhardt | |
| 6,051,216 A | 4/2000 | Barr et al. | |
| 6,054,517 A | 4/2000 | Spaulding et al. | |
| 6,063,398 A | 5/2000 | Gueret | |
| 6,074,654 A | 6/2000 | Drechsler | |
| 6,103,249 A | 8/2000 | Roulier | |
| 6,106,820 A | 8/2000 | Morrissey | |
| 6,111,055 A | 8/2000 | Berger et al. | |
| 6,156,325 A | 12/2000 | Farer | |
| 6,156,804 A | 12/2000 | Chevalier | |
| 6,165,971 A | 12/2000 | Oppenlander | |
| 6,177,523 B1 | 1/2001 | Reich | |
| 6,180,123 B1 | 1/2001 | Mondet | |
| 6,183,760 B1 | 2/2001 | Travkina et al. | |
| 6,184,196 B1 | 2/2001 | Bazin | |
| 6,190,673 B1 | 2/2001 | Guskey | |
| 6,203,780 B1 | 3/2001 | Arnaud | |
| 6,214,329 B1 | 4/2001 | Brieva | |
| 6,251,375 B1 | 6/2001 | Bara | |
| 6,254,877 B1 | 7/2001 | de la Poterie | |
| 6,268,466 B1 | 7/2001 | MacQueen et al. | |
| 6,280,846 B1 | 8/2001 | Darby | |
| 6,287,552 B1 | 9/2001 | Tournilhac | |
| 6,348,563 B1 | 2/2002 | Fukuda | |
| 6,365,139 B2 | 4/2002 | Travkina et al. | |
| 6,372,235 B1 | 4/2002 | Livoreil | |
| 6,399,081 B1 | 6/2002 | Nakanishi | |
| 6,402,408 B1 * | 6/2002 | Ferrari | 401/64 |
| 6,423,324 B1 | 7/2002 | Murphey | |
| 6,432,391 B1 | 8/2002 | Bara | |
| 6,432,907 B1 | 8/2002 | Skold | |
| 6,469,131 B2 | 10/2002 | Lawson | |
| 6,475,500 B2 | 11/2002 | Vatter | |
| 6,479,686 B2 | 11/2002 | Nakanishi | |
| 6,482,400 B1 | 11/2002 | Collin | |
| 6,488,919 B1 | 12/2002 | Murphy et al. | |
| 6,491,931 B1 | 12/2002 | Collin | |
| 6,497,861 B1 | 12/2002 | Wang et al. | |
| 6,503,077 B2 | 1/2003 | Pavlin et al. | |
| 6,503,522 B2 | 1/2003 | Pavlin | |
| 6,503,880 B1 | 1/2003 | Skold | |
| 6,555,099 B2 | 4/2003 | Guskey et al. | |
| 6,592,857 B2 | 7/2003 | Lawson | |
| 6,835,374 B2 | 12/2004 | Parekh et al. | |
| 6,869,594 B2 | 3/2005 | Ferrari | |
| 6,960,339 B1 | 11/2005 | Ferrari | |
| 7,208,143 B2 | 4/2007 | Bertz et al. | |
| 2001/0014312 A1 | 8/2001 | Nakanishi | |
| 2001/0031280 A1 | 10/2001 | Ferrari et al. | |
| 2001/0036914 A1 | 11/2001 | Philippe et al. | |
| 2002/0019510 A1 | 2/2002 | Orth et al. | |
| 2002/0035237 A1 | 3/2002 | Lawson et al. | |
| 2002/0037993 A1 | 3/2002 | Lawson et al. | |
| 2002/0058053 A1 | 5/2002 | Nakanishi | |
| 2002/0081323 A1 | 6/2002 | Nakanishi | |
| 2002/0102225 A1 | 8/2002 | Hess | |
| 2002/0114771 A1 | 8/2002 | Nakanishi | |
| 2002/0119171 A1 | 8/2002 | Gruning | |
| 2002/0131947 A1 | 9/2002 | Nakanishi | |
| 2002/0150602 A1 | 10/2002 | Livoreil | |
| 2002/0159964 A1 | 10/2002 | Nakanishi | |
| 2002/0168335 A1 | 11/2002 | Collin | |
| 2003/0044367 A1 | 3/2003 | Simon | |
| 2003/0069388 A1 | 4/2003 | Lawson et al. | |
| 2003/0161807 A1 | 8/2003 | Lemann | |
| 2004/0151686 A2 | 8/2004 | Lemann | |
| 2004/0156804 A1 | 8/2004 | Poterie et al. | |
| 2004/0202626 A1 | 10/2004 | Wang et al. | |
| 2005/0065251 A1 | 3/2005 | Candau | |
| 2005/0169875 A1 | 8/2005 | Wang et al. | |

FOREIGN PATENT DOCUMENTS

| | | |
|---|---|---|
| DE | 19750246 | 5/1999 |
| EP | 0 388 582 | 9/1990 |
| EP | 0 522 624 A1 | 1/1993 |
| EP | 0820764 | 1/1998 |
| EP | 0295886 | 12/1998 |
| EP | 0958804 | 11/1999 |
| EP | 0958805 | 11/1999 |
| EP | 1 018 332 A2 | 7/2000 |
| EP | 1031342 | 8/2000 |
| EP | 1048282 | 11/2000 |
| EP | 1 068 856 A1 | 1/2001 |
| EP | 1068855 A1 | 1/2001 |
| EP | 1090627 | 4/2001 |
| EP | 1095959 | 5/2001 |
| FR | 2785179 | 5/2000 |
| FR | 2816506 | 5/2002 |
| GB | 1117129 | 6/1968 |
| GB | 1194901 | 6/1970 |
| GB | 1194902 | 6/1970 |
| GB | 1273004 | 5/1972 |
| GB | 2147305 | 5/1985 |
| GB | 2196978 | 5/1988 |
| JP | 56-166276 | 12/1981 |
| JP | 62-061911 | 3/1987 |
| JP | 02-88511 | 3/1990 |
| JP | 04-221306 | 8/1992 |
| JP | 04-346909 | 12/1992 |
| JP | 09-020631 | 1/1997 |
| JP | 09-255560 | 9/1997 |
| JP | 10-212213 | 8/1998 |
| JP | 2000-038314 | 2/2000 |
| JP | 2000-086427 | 3/2000 |

| JP | 2000-086429 | 3/2000 |
| JP | 2000-086438 | 3/2000 |
| WO | WO 98/17705 | 4/1998 |
| WO | WO 98/35649 | 8/1998 |
| WO | WO98-47470 | 10/1998 |
| WO | WO00-27350 | 5/2000 |
| WO | WO 00/40216 | 7/2000 |
| WO | WO02-49601 | 6/2002 |
| WO | WO02-056845 | 7/2002 |
| WO | WO02/102322 | 12/2002 |

OTHER PUBLICATIONS

Handbook of Cosmetic Science and Technology, 1994, Elsevier Advaced Technology, 1st edition, p. 19.

Xuzhong Luo, et al. Self-Assembled Organogels formed by Monoalkyl Derivatives of Oxamide, 2000, Chemical Communications, 2091-2092.

Terech, P., Low Molecular Weight Organogelators, 1997, Specialist Surfactants, 208-268.

http://www.smartskincare.com/skinprotection/sunblocks/sunblock_avobenzone.html; SmartSkinCare.com; Chemical UVA sunscreen/sunblock agent: Avobenzone (Parsol 1789, Eusolex 9020, Escalol 517; Sep. 2009.

http://www.clearcoproducts.com/dimethicones.html; Clearco 1.5cSt.PURE; Silicone Fluid (Decamethyltetrasiloxane); Product Information; Super Low-Viscosity Volatile Silicone: Decamethyltetrasiloxane (CAS 141-62-8) INCI Name: Dimethicone; 6 pages; Sep. 2008.

International Cosmetic Ingeredient Dictionary and Handbook; Ninth Edition; vol. 1; Ethylene/Acrylic Acid/VA Copolymer; Ethylene Dioleamide; Monographs; p. 606; 2002.

Goldschmidt AG; Goldschmidt Personal Care; Degussa; Creating Essentials; TAGAT® CH40; TAGAT® CH60; TAGAT® L2; TAGAT® O2V; TAGAT® S; TAGAT® S2; Mild nonionic surfactants, solubilizers; pp. 1-5; May 2003.

USPTO Office Action; Board of Patent Appeals and Interferences; Decision on Appeal; *Ex Parte Patricia Lemann*; Appeal 2008-0054271; U.S. Appl. No. 10/312,083, filed Mar. 26, 2003; Technology Center 1600; Decided:2 Jun. 19, 2009; issued to L'Oreal's Attorney, Finnegan, Henderson, Farabow, Garrett & Dunner LLP; Mailing Date. Jun. 19, 2009. Estee Lauder did not become aware of this Document until on or about Feb. 26, 2010.

* cited by examiner

STABLE COSMETIC EMULSION WITH POLYAMIDE GELLING AGENT

This application claims priority of U.S. 60/388,154, filed on Jun. 11, 2002, and U.S. Ser. No. 09/886,918, filed on Jun. 21, 2001, the contents of each of which are incorporated herein by reference.

FIELD OF THE INVENTION

The invention relates to a cosmetic and personal care gel product that is gelled using a polyamide as a gelling agent in the oil phase. More specifically, the invention relates to a stable emulsion based compositions comprising a polyamide gelling agent in the oil phase.

BACKGROUND OF THE INVENTION

Many gelled cosmetic emulsions rely on gellants, waxes, fillers, heavy oils, and plasticizers for developing the structure to make a gel or stick composition. The structure built by these agents and materials give the product a balance of rigidity and firmness depending on the desired product. For example, the structure of lipstick is traditionally formed by a blend of wax and oil. However, these adjuvants, particularly waxes, have a disadvantage in that they contribute to opacity which diminishes the color of the pigment. The product therefore, has a dull, lackluster and pale appearance. To overcome this problem, enhanced amounts of pigment are added to the composition. Another drawback to the addition of wax is that it adheres poorly to the skin and compromises the longevity of wear of the product. For example, many commonly used cosmetic products, such as foundation, concealer, eyeliner, and lipstick, which contain these materials, are subject to fading, smudging, and flaking. Such products also have a matte appearance that is not always desirable. In addition, other adjuvants such as heavy oils can feel uncomfortable on the skin and have a distinct oily feel that may also be unpleasant. Therefore, to address these issues, alternative gelling agents have been sought and specific polyamides have been used to gel cosmetic products.

The use of polyamides in cosmetic products has been known. For example, polyamide resins have been used in an anhydrous lipstick as disclosed in U.S. Pat. No. 3,148,125. The method of making polyamides is disclosed in, for example, U.S. Pat. No. 2,450,940. The polyamide resin has also been used in a deodorant or antiperspirant gel or stick as disclosed in U.S. Pat. Nos. 4,275,054 and 5,500,209 because of its odor absorbing properties. None of these references, however, discloses a stable emulsion gelled with a stable polyamide. The stick, soft gel, or clear gel compositions disclosed in, for example, U.S. Pat. Nos. 6,051,216, 5,603,925, and 5,998,570 and European Patent Application Nos. EP 1 068 855 and EP 1 068 856 are unstable emulsions, single phase compositions, or use a siloxane based polyamide. The siloxane polyamides have been developed because of their alleged ability to, in addition to gel the composition, provide a less tacky composition. However, the siloxane based polyamides are not compatible with a wide variety of oils, for example, hydrocarbon oils (except low molecular weight), and because they are less tacky, their adhesion properties are significantly impaired, making them less desirable in products that require minimally an initial phase of adhesion during the application of the product to the skin or hair. Therefore, it is desirable to use other polyamides in cosmetic emulsion systems because products such as mascara, for example, need a certain degree of tackiness when being applied but afterwards, upon drying the tackiness of the mascara needs to transition to a comfortable feel on the lashes. Until now, it has not been known to fine-tune the tacky nature of a cosmetic dual phase product containing the polyamide resin as a gelling agent. The compositions heretofore have either been too tacky or not tacky enough for products that need to exhibit varying degrees of tackiness over time and during their use. Thus, the emulsions of the present invention gelled with a polyamide based gelling system that has heretofore not been known. A need for a stable cosmetic emulsion gelled by a stable polyamide resin system that adheres to the skin and functions in a variety of cosmetic emulsion systems still remains. The emulsion system of the present invention is also desirable because it allows water-soluble ingredients to be incorporated into the product containing the emulsion.

SUMMARY OF THE INVENTION

The invention relates to gelled cosmetic compositions, and specifically, oil-in-water or water-in-oil emulsions, which comprises at least one alkylene oxide containing emulsion stabilizer and at least one non-siloxane based polyamide resin. The prepared emulsions, while they are not themselves clear, are substantially transparent after application to the skin. Use of the polyamide resin as a gelling agent per se is not new, however, its incorporation into the color compositions of the present invention containing a $C_{1-5}$ alkylene oxide, for example, ethylene oxide or propylene oxide, as an emulsion stabilizer is surprising. The cosmetic emulsions of the present invention also comprise a color component present in an amount greater than about 2.0 percent by weight of the composition. The ability to gel a color cosmetic emulsion with the polyamide resin as the primary gelling agent is particularly challenging because the polyamide is very polar and emulsions containing large quantities of polyamide tend to be tacky and are difficult to stabilize in the presence of colorants.

The gelling system for the composition comprises at least one polyamide resin that has a moiety attached thereto. The moiety contains at least one linking hetero-atom that has an electronegativity of greater than 2.5, and preferably, between 2.5 and 4.0, and is present as an acid, amine, ester, tertiary amide terminal end group, and the like. The terminal end group is end-capped and/or grafted. In addition, the gelling system has at least one resin stabilizer containing an atom that also has an electronegativity of greater than 2.5, and preferably, between 2.5 and 4.0. The resin stabilizer is preferably present when the terminal end group is tertiary amide. Examples of atoms are carbon, nitrogen, oxygen and the like. The compositions of the present invention are virtually non-sweating even in an emulsion containing solvents that are hydrophobic such as for example, hydrocarbon oils and silicone oils. This is especially beneficial when the compositions contain a colorant component and are in the form of a lipstick because they can be exposed to elevated temperatures, e.g., greater than 45° C. or 50° C. Finally, the cosmetic emulsion preferably contains a solid surfactant in an amount of about 0.01 to about 20 percent.

The present invention also includes methods of making the emulsion systems of the present invention which can include multiple emulsion systems. The emulsion products are especially transparent and transfer resistant when they are applied to the skin and allowed to dry. Therefore, the compositions containing these emulsions have an enhanced brightness and clarity with respect to their color on the skin after application thereon due to the transparent film that adheres to the skin without being tacky. The emulsion systems of the present invention dry faster than other polyamide containing systems, and are long wearing even after the water evaporates. In addition, gels and sticks made with the emulsion system of the present invention are less brittle, experience a substantial lack of syneresis, and have a creamier texture.

DETAILED DESCRIPTION OF THE INVENTION

The gelling system of the present invention is at least one non-siloxane based polyamide resin and at least one $C_{1-5}$ alkylene oxide containing emulsion stabilizer. The polyamide resin as used herein is defined to be a polymer having recurring units of amide groups as an integral part of the main chain of the polymer and a terminal end group of tertiary amide, acid, amine, or ester. The polyamides are characterized as thermoplastics as opposed to thermosets, and have a resonance structure, based on the conjugated system, that increases its hydrophilic nature, and tendency towards forming hydrogen bonds. The polyamide gelling agent can be used to produce a soft gel or a stick composition in an emulsified system. However, to maintain its stability as a gelling agent, it is preferable that the polyamide resin not be extensively cross-linked by hydrogen bonds. Accordingly, the gelling system of the present invention is at least one polyamide resin having a moiety containing at least one linking hetero-atom having an electronegativity greater than 2.5, and preferably, between 2.5 and 4.0, and at least one resin stabilizer containing an atom also having an electronegativity greater than 2.5, and preferably, between 2.5 and 4.0. The linking hetero-atom is end-capped or grafted at the end of the polyamide resin such that in a preferred embodiment, the moiety is a terminal end group of tertiary amide, ester, amine, acid or the like, and mixtures thereof. Preferably, the terminal end group is tertiary amide. The resin stabilizer preferably is represented by the structure $R_1XR_2$, where X is a polar atom such as, for example, halogen, oxygen or nitrogen, and where $R_1$ is hydrogen (e.g., $XR_1$) or $R_2$, and $R_2$ is a fatty chain having a functional group of, for example, amine, amide, hydroxyl, phospholipid groups, containing, for example, 8 to 22, preferably 10 to 20, and more preferably, 16 to 18 carbon atoms. The activity of the resin stabilizer is enhanced by the resonance structure of the polyamide resin system.

Based on tertiary amides, esters, amines, or acids, the polyamides used in the present invention are water insoluble. The polyamide is available in a solid form of 100 percent polyamide or as a percentage of polyamide in solvents such as, for example, mineral oil, usually about 80 percent. Examples of commercially available polyamides which are useful in the present invention are Versamid 1655, by Cognis (formerly Henkel Corporation), Ambler, Pa. which is prepared from dimers of $C_{18}$ unsaturated fatty acids which are partially hydrogenated, azelaic acid (nonanedioic acid), ethylene diamine, hexamethylene diamine and stearic acid, Unirez and Uniclear, a series of polyamides from Arizona Chemicals Corporation, Jacksonville, Fla. or Elvamide from DuPont, DE a terpolymer of nylon 6, nylon 66, and nylon 610. Additional polyamides are disclosed in U.S. Pat. Nos. 4,820,765, 5,719,255, 5,807,968, 6,111,055, and 6,054,517, the contents of which are incorporated herein by reference. These references fail to recognize the ability to make a stable emulsion product, and thus, fail to recognize the benefits of a water containing cosmetic emulsion incorporating a polyamide gelling agent and an $C_{1-5}$ alkylene oxide containing surfactant. For example, U.S. Pat. No. 5,783,657 is an anhydrous system, and U.S. Pat. No. 5,998,570 discloses that water is preferably removed when forming the polyamide, and compositions comprise a nonaqueous liquid as solvent, preferably a low-polarity liquid. Tertiary amide terminated polyamides are disclosed in, for example, U.S. patent application Ser. Nos. 2002/0035237 and 2002/0019510, and U.S. Pat. No. 6,268,466. However, none of these references discloses the ability to achieve a substantially non-sweating emulsion with the gelling system of the present invention.

An ester terminated polyamide (ETPA) of U.S. Pat. No. 6,111,055 comprises molecules of the formula (1),

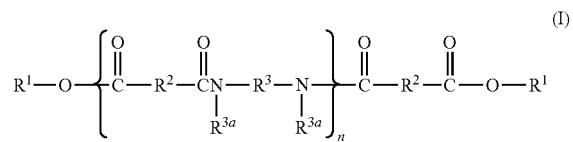

wherein n designates a number of repeating units such that ester groups constitute from 10% to 50% of the total of the ester and amide groups; $R^1$ at each occurrence is independently selected from an alkyl or alkenyl group containing at least 1 carbon atom, preferably at least 4 carbon atoms; $R^2$ at each occurrence is independently selected from a $C_{4-42}$ hydrocarbon group with the proviso that at least 50% of the $R^2$ groups have 30-42 carbon atoms; $R^3$ at each occurrence is independently selected from an organic group containing at least two carbon atoms in addition to hydrogen atoms, and optionally containing one or more oxygen and nitrogen atoms; and $R^{3a}$ at each occurrence is independently selected from hydrogen, $C_{1-10}$ alkyl and a direct bond to $R^3$ or another $R^{3a}$ such that the N atom to which $R^3$ and $R^{3a}$ are both bonded is part of a heterocyclic structure defined in part by $R^{3a}$—N— $R^3$, such that at least 50% of the $R^{3a}$ groups are hydrogen.

However, it has been surprisingly found that when the number of carbon atoms in the $R^1$ group is increased above 4, and preferably has at least about 10 carbon atoms, more preferably at least about 12 carbon atoms, then ETPA is an excellent gellant for aliphatic hydrocarbon. The upper range for the number of carbon atoms in the $R^1$ group is not particularly critical, however preferably the $R^1$ group has less than or equal to about 24 carbon atoms, and more preferably has less than or equal to 22 carbon atoms. $R^1$ groups having about 16-22 carbon atoms are highly preferred. The identity of $R^1$ at any occurrence is independent of the identity of $R^1$ at any other occurrence.

The $R^2$ group in formula (1) is suitably a hydrocarbon containing 4 to 42 carbon atoms. A preferred $R^2$ group contains 30-42 carbon atoms (i.e., is a $C_{30-42}$ group), and at least 50% of the $R^2$ groups in an ETPA gellant preferably have 30-42 carbon atoms. Such $R^2$ groups are readily introduced into an ETPA when the gellant is prepared from polymerized fatty acid, also known as dimer acid. Typical unsaturated fatty acids used to form polymerized fatty acid include oleic acid, linoleic acid, linolenic acid, etc. Tall oil fatty acid, which is a mixture containing long-chain unsaturated fatty acids obtained as a byproduct of the wood pulping process, is preferred for preparing polymerized fatty acid useful in ETPA formation.

In one embodiment, all of the $R^{3a}$ groups in an ETPA gellant are hydrogen, so that $R^3$ alone joins the two nitrogen atoms shown in the formula $(R^{3a})$—$R^3$—$N(R^{3a})$. In this case, the $R^3$ group contains at least two carbon atoms, and optionally oxygen and/or nitrogen atoms, in addition to any hydrogen atoms that are necessary to complete otherwise unfilled valencies of the carbon, oxygen and nitrogen atoms. In a preferred embodiment, $R^3$ is a hydrocarbon group, having 2 to about 36 carbon atoms, preferably having 2 to about 12 carbon atoms, and more preferably having 2 to about 8 carbon atoms.

The water phase of the cosmetic emulsion of the present invention comprises about 0.05 to 90.0 percent, and preferably 1.0 to 70.0 percent by weight of the emulsions. While the water phase is primarily water, it can take the form of a variety of aqueous solutions such as rose water, tea, and the like. Therefore, the water phase is well suited to deliver water-soluble actives and other water dispersible agents, such as for example, film-formers, surfactants, and emollients. The non-ueous phase can include any type of cosmetically acceptable volatile or non-volatile oil including oily esters depending on the application of the product and the degree of gelling desired. Examples include, but are not limited to, hydrocarbon oil such as isododecane, silicone oils such as cyclomethicone, polyorganosiloxanes such as phenyl-methicones and dimethicones, castor oil, and hydrogenated vegetable oil. Preferably, in a mascara, the oil is volatile, such as for example, a volatile hydrocarbon oil or silicone oil; while a lipstick is a mixture of both volatile and non-volatile oils, and the amounts of each depends on the type of lipstick desired. Suitable non-volatile hydrocarbons include, but are not limited, to isoparaffins, squalane, or petrolatum, or mixtures thereof. Regardless of the amount of volatile and/or non-volatile oil, the entire oil phase is present in an amount of about 5 to about 95 percent, preferably 10 to 80 percent by weight of the composition, and more preferably about 10 to 40 percent.

The emulsions of the present invention are prepared by adding a gelling sufficient amount of the polyamide resin to the oil phase. In one embodiment of the invention, a gelling sufficient amount of the resin stabilizer is added along with the polyamide resin as the gelling system. This is preferable when the terminal end group is tertiary amide. The amount of polyamide resin used in the present invention is from about 1 to about 90 percent, preferably about 2 to 40 percent by weight of the composition. The amount of polyamide is a "gelling sufficient amount" and as used herein means an amount of polyamide in the oil phase to bring about an increase in the viscosity of the emulsion; preferably the viscosity increases by 25 percent, more preferably by 50 percent, and most preferably by 75 percent. This increase in viscosity is sufficient to form a thickened gel or form a solid having the hardness of a stick as the thickness of gels and sticks are known in the art. At lower levels, the polyamide aids in forming a gel, whereas, higher levels are used to make stick products. Although it is difficult to quantitatively distinguish between a cosmetic gel and stick, a gel is, in general, more viscous than a liquid; but, it is not as rigid or self-supporting as a stick. It is accepted by one of ordinary skill in the art that a gel maintains a certain degree of deformity, whereas, the stick is free-standing and is substantially rigid.

While the resin stabilizer functions to stabilize the polyamide, and therefore, the gelling of the system, it has also been found that the presence of an emulsion stabilizer such as, for example, an ethylene oxide containing surfactant, stabilizes the emulsion system. Accordingly, an optional component of the present invention is the $C_{1-5}$ alkylene oxide containing emulsion stabilizer. It is surprisingly discovered with the present invention that a stable emulsion comprising the polyamide resin as the gelling agent can be achieved. Although, it is known to gel alcoholic based systems and oil based systems with the polyamide resin, until now, these systems have primarily been single phase. Moreover, even when emulsions are prepared, there can be a tendency to experience stability problems. In particular, stable dual phase compositions, and especially, stable cosmetic emulsions, have not been known to contain a polyamide gelling agent, especially, a non-siloxane based polyamide gelling agent, as the polyamide experiences stability problems in the presence of solvents that are hydrophobic. The non-siloxane based polyamides are known to be tacky. Therefore, their use is limited and most appropriate for coatings, paints, inks, epoxies, adhesives and the like. Their use in cosmetics has also been limited primarily to single phase systems such as anhydrous lipsticks and deodorants. However, the ability to formulate these types of cosmetics is quite different than the challenges presented by formulating a cosmetic emulsion, especially a stable emulsion in a color cosmetic. Thus, when used as a gelling agent in an emulsion, the stability of the polyamide can be an issue. The ability to formulate cosmetic emulsions that are essentially non-sweating is difficult especially when the cosmetic contains hydrophobic solvents.

The emulsion stabilizers aid the resin stabilizer in rendering the polyamide resin compatible in the dual phase system, and enhance not only the stability of the emulsion containing the polyamide resin as the gelling agent, but may also affect the gelling activity of the polyamide resin in the dual phase system. In other words, the emulsion stabilizer directly functions to stabilize the emulsion and the resin stabilizer directly functions to stabilize the polyamide resin. But, in addition, each of these functions is inter-related. Because the polyamide resin is water-insoluble when used as a gelling agent in the emulsion, stability problems are known to arise. In particular, agglomeration occurs or the phases separate in a short time, for example, in about few hours to about a few months. However, the present invention has discovered that this problem can be remedied with the emulsion stabilizer which can be present in the oil phase, the water phase, or both. As a result, the polyamide resin is rendered compatible in the emulsion stabilizer at room temperature and/or at elevated temperature. In addition, the emulsion is stable without any phase separation for about 6 months, preferably about 1 year, and more preferably about two years as measured by accelerated stability testing methods, known to one of ordinary skill in the art.

The ethylene oxide containing surfactant is known to be temperature sensitive, and therefore, when used in emulsions, experiences stability problems. Considering the difficulty of formulating a cosmetic emulsion, and in addition, the difficulty of using the polyamide gelling agent in a substantially non-sweating emulsion, it is surprising that greater emulsion stability is achieved using the ethylene oxide containing emulsifier. While not wishing to be bound to any particular theory, it is believed that emulsion stability, and thus, enhanced gelling is achieved with the ethylene oxide containing emulsifier because it is capable of hydrogen bonding with the polyamide gelling agent. This is further enhanced by the gelling system of the present invention. The emulsion stabilizer can be a single surfactant or a combination of surfactants.

Preferably, the emulsion stabilizer is an ethylene oxide or propylene oxide. More preferably, the emulsion stabilizer of the present invention is primarily ethylene oxide containing surfactants, ethoxylated alcohols, and emulsifiers such as polyethlyene glycol esters. Specifically, the emulsion stabilizer can be cetyl dimethicone copolyol/polyglyceryl-4 isostearate/hexyl laurate, PEG-30 dipolyhydroxystearate, sorbitan tristearate, glyceryl stearate/PEG-100 stearate, glyceryl olivate, polysorbate 20, stearic acid, or laureth-7. Examples of solvents, include but are not limited to, emollients such as low polarity liquid emollients, straight chain and branched fatty alcohols, cetyl alcohol and isocetyl alcohol, monohydric or polyhydric alcohols, such as propylene glycol and dipropylene glycol, fatty acid esters, such as cetyl acetate/acetylated lanolin alcohol.

In yet another embodiment, the emulsion is stabilized by the addition of nitrogen containing soap-based emulsifiers, or alkanolamides of fatty acids, preferably, lauramide MEA or stearamide MEA, and derivatives thereof. The lipstick containing, for example, lauramide MEA (monoethanolamine), is particularly effective in providing stability against the development of syneresis even when the lipstick is in the form of a water-in-oil emulsion.

Other features of the emulsions of the present invention include their substantial transparency when applied to the skin, good adherance to the skin without being tacky, and their substantial transfer resistance. The emulsions can be wax-free because the need to build structure with large amounts of wax is eliminated by the presence of the polyamide gelling agent. The use of the polyamide gelling agent in the presence of the water phase of an emulsion system is an improvement over traditional wax-based emulsions because wax forms an opaque oil phase (i.e., when light scatters off of the wax microstructure). The opaque oil phase renders the color less brilliant because it interferes with the true appearance of the color even when applied to the skin. Further, wax has poor adhesion properties to the skin. Therefore, it is not long wearing. Although it is widely used in mascara, lipstick, and other products, the presence of wax can cause these products to transfer easily from the skin to other unwanted substrates (e.g., clothes, cups), the color fades quickly, and smudging and flaking are common problems as well. However, the polyamide gelled emulsions of the present invention adhere well to the skin. Strong adherance to the keratinous substrate is believed to be by hydrogen bonds between the polyamide and the keratin. The surprising benefit of the present invention is the ability to achieve opposing properties of adherance to the skin without a tacky feeling to the emulsion product. It is commonly found that measures taken to increase the adhesiveness of a composition result in a corresponding increase in the tackiness of the composition. However, the emulsions of the present invention overcome this mutual exclusivity and have both a pleasant creamy feel and good adherance to the skin.

In addition, to gelling an emulsion that is substantially non-sweating, the polyamide functions to maximize the color integrity because the emulsion is substantially transparent or semi-transparent when applied and allowed to dry on the skin. As used herein, "substantially transparent" means that greater than 75 percent light can be transmitted through the oil phase; preferably, 80 percent; and more preferably, 90 percent. Thus, the term "transparency" as employed herein refers to invention cosmetic stick products which have translucent or transparent light transmitting properties, and refers to a clear body which has the property of transmitting light without appreciable scattering, so that objects beyond are entirely visible. The term "translucent" refers to a body which is partly transparent. The body admits and diffuses light, so that objects beyond are visible but cannot be clearly distinguished. The term "opaque" refers to a body which is impervious to visible light. An opaque body lacks any degree of transparency.

The cosmetic emulsions of the present invention also include a colorant component comprising one or more colorants. The term "colorant" as used herein includes pigments, dyes, stains, colorants, combinations thereof, and the like. Any cosmetically acceptable colorant can be used in the emulsions of the present invention. The color of the product after addition of the colorant is intense and bright upon application to the skin. Suitable organic pigments can be, for example, natural pigments, monomeric and polymeric synthetic pigments, or combinations thereof. Exemplary organic pigments include, but are not limited to, phthalocyanine blue and green pigments and azo-type red pigments such as naphthol red pigment. Other suitable aromatic pigment compounds include, but are not limited to, azo, triphenyl methane, indigo, anthraquinone, and xanthine dyes which are referred to as D&C, and FD&C pigments, such as for example, FD&C blue No. 1, FD&C green No. 5, FD&C red No. 40, and FD&C yellow No. 5. Also useful are lakes which are pigments formed by the precipitation and absorption of organic dyes in an insoluble base, such as alumina, barium, or calcium hydrates. Particularly preferred lakes are primary FD&C or D&C Lakes and blends thereof. Colorant concentrations will vary depending upon the desired color or tint of the cosmetic product, but the colorant component generally will be greater than 2.0 percent, and preferably, greater than 5.0 percent by weight of the total composition.

The colorant can also be an inorganic pigment. The inorganic pigment is present in low amounts and preferably, the inorganic pigment has a small particle size, for example, a submicron particle size that will disperse and permit the cosmetic product to maintain a clear appearance. Examples of inorganic pigments include, but are not limited to, iron oxides (yellow, red, brown or black), ultramarines, chromium hydroxide green, chromium oxide, titanium dioxide (white), ferric ferrocyanide, ferric ammonium ferrocyanide, and mixtures thereof. The pigments can be ground by, for example, a rolling mill, or alternatively, the pigments can be purchased pre-ground in a blend containing, for example, water, polysaccharides, and black iron oxide. The ability to incorporate dyes, pigments and colorants is challenging in an emulsion system, especially one that contains the non-siloxane based polyamide as the gelling agent, and the ethylene oxide containing emulsion stabilizer. However, surprisingly, the color of the cosmetic emulsions of the present invention, after application to the skin, provides maximum color impact. The color is deep, brilliant and crisp.

The active ingredients incorporated in the emulsions of the present invention having a polyamide as the gelling agent preferably do not include antiperspirant actives especially those that are acidic metal salts. Examples of actives that can be used in the present invention include, but are not limited to, sunscreen actives, whitening agents, such as for example, antioxidants, antimicrobials, analgesics, anesthetics, antiacne agents, antidermatitis agents, antipruritic agents, antiinflammatory agents, antihyperkeratolytic agents, anti-dry skin agents, antipsoriatic agents, antiseborrheic agents, antiaging agents, antiwrinkle agents, self-tanning agents, woundhealing agents, corticosteroids, or hormones. The incorporation of the active in the formulation is determined by its solubility and/or stability in combination with non-siloxane polyamide gelled emulsions of the present invention. The term "sunscreen" as used herein refers to any material which is capable of protecting skin from ultraviolet radiation having a wavelength of from about 280 to about 400 nm, by effectively absorbing such radiation, and/or reflecting or scattering such radiation away from the surface of skin. Examples of sunscreens with which the compositions of the present invention can be combined in this context are titanium dioxide, zinc oxide, benzophenones, octyl dimethyl PABA, amyldimethyl PABA, octyl methoxycinnamate, 2-ethoxy p-methoxycinnamate, oxybenzone, homosalate, phenyl salicylate, avobenzene, glyceryl p-aminobenzoate, ethyl-p-glycosylimido benzoate and the like. In a formulation, the sunscreen agent is used in the amounts normally used for that agent. Preferably, the active is non-acidic. The selection of the mode of delivery for additional active ingredients, however, is limited to the mode of delivery chosen for the compositions.

The cosmetic product can be, but is not limited to, a lipstick, lip gloss or other lip product, a solid, or gel fragrance or perfume product, cleanser, toner, an eye product, such as a mascara, eyeliner or an eye gel, compact emulsion foundation, concealer, moisturizing skin lotion or cream, hair stick or gel, and any other makeup, or skin or sun care product that is in a gel or stick form. In a preferred embodiment, the product is a mascara or lipstick product. The base of the lipstick or mascara has sufficient clarity such that the color is bright and luminous, i.e., they are transparent, semi-transparent, or translucent. The products of the present invention are long wearing, non-smudging, and non-flaking.

Further, the clear cosmetic product can contain other optional components as long as they do not interfere with the gelling properties of the polyamide. Examples include, but are not limited to, one or more preservatives such as, for example, propyl paraben, butyl paraben, mixtures thereof, or isoforms thereof, as well as butyl hydroxy toluene or butyl hydroxy anisol (BHT or BHA); fragrances (such as pinene); flavoring agents; waterproofing agents (such as PVP/eicosene copolymer); surfactants, such as silicone copolyols or fatty acid glycerol esters; and oil-soluble actives, such as tocopherol and its derivatives or retinol and its derivatives; and the like.

The method of preparing the emulsions of the present invention entails basic steps known in the art for preparing emulsions. The non-siloxane based polyamide or the polyamide resin with an electronegative moiety of greater than 2.5 and the resin stabilizer, along with the other ingredients in the oil phase may be prepared separately but are combined or added to the oil phase before combining with the aqueous phase to make the emulsion. The present emulsions, containing the gelling system, can be prepared with the polyamide as the primary gelling agent in the gelling system or with other naturally derived or synthetic gellants or thickening agents, known and commonly used by one skilled in the art, such as for example, cetyl dimethicone copolyol, acrylates copolymer, dextrin fatty acid esters, carbopols, dibenzyl monosorbitol acetal, polyethylene wax, beeswax, carnauba wax, candilla wax, bayberry wax, rice wax, acylglutamic acid diamide, esters, fatty alcohols, and the like can be used in the oil phase of the present invention. Preferably, however, the compositions of the present invention are wax-free.

The invention is further illustrated by the following non-limiting examples.

EXAMPLES

I. Lipstick with Polyamide Gelling Agent

| Material | Weight % |
| --- | --- |
| Phase I | |
| Polyamide resin | 18.0 |
| Isocetyl alcohol | 22.0 |
| Stearyl alcohol | 4.0 |
| Lauramide MEA | 3.0 |
| Propylene carbonate | 3.8 |
| Laureth-7 | 4.0 |
| Isopropyl alcohol | 2.0 |
| Glycerin | 3.0 |
| Cyclomethicone | 4.0 |

-continued

| Material | Weight % |
| --- | --- |
| Acrylates copolymer | 0.2 |
| Cetyl dimethicone copolyol/Polyglyceryl-4 isostearate/Hexyl laurate | 2.0 |
| Phase II | |
| Dimethicone | 1.0 |
| Castor oil | 4.0 |
| Hydrogenated vegetable oil | 0.8 |
| Iron oxide | 0.6 |
| FD&C Blue #1 | 0.3 |
| FD&C Yellow #5 | 1.0 |
| Bismuth oxychloride | 4.0 |
| Mica/Titanium Dioxide/Carmine/Methicone | 0.9 |
| D&C Red #7 | 3.0 |
| Phase III | |
| Water | 18.5 |

The lipstick is prepared by combining Phase I ingredients together and heating them to about 99° C. for about 2 hours. Phase II ingredients are combined and ground in a homogenizer at about 3000 rpm for about 10 minutes. The homogenized Phase II ingredients are added to Phase I and together the combination is heated to 80° C. Phase III is added to the combined Phase I and Phase II ingredients at a temperature of about 80° C. by mixing. Adjust pH of combination with to about 7.35. The lipstick can be made by pouring the combination into a lipstick mold or by following any known technique for making a lipstick.

II. Oil in Water Mascara with Polyamide Gelling Agent

| Material | Weight % |
| --- | --- |
| Phase I | |
| Polyamide resin | 10.00 |
| Sorbitan Tristearate | 1.00 |
| Glyceryl Stearate/PEG-100 Stearate | 1.00 |
| Stearic Acid | 4.00 |
| Dioctyl Adipate/Octyl Stearate/Octyl Palmitate | 1.00 |
| Stearamide MEA Stearate | 3.00 |
| Phase II | |
| Dimethicone | 2.50 |
| Cyclomethicone | 5.00 |
| Isododecane | 11.00 |
| Ethanol | 0.50 |
| Phase III | |
| Water | 22.50 |
| Silica | 1.00 |
| Polysorbate 20 | 2.00 |
| Acacia Gum | 0.25 |
| Phase IV | |
| Water | 10.45 |
| Black iron oxide | 8.00 |
| Polyvinylpyrrolidone | 1.00 |
| Phase V | |
| Water | 8.00 |
| Shellac | 2.00 |
| Acrylic copolymer | 5.00 |
| Preservatives | 0.80 |

Combine Phase I ingredients and heat to about 90° C. until solids are melted. Add Phase II ingredients to Phase I ingredients and maintain heat at about 60° C. Heat Phase III ingredients to about 60° C. and combine with Phase IV ingredients.

Add combined Phase III and IV ingredients to Phase I and II ingredients by mixing. Add Phase V ingredients to the mixture and adjust pH to about 7.35. The mascara is tested for stability by storing the mascara at 50° C. Accelerated stability data is measured using a Brookfield rheometer. An initial viscosity measurement is 49.5. Six-week viscosity measurement is 45.0 and predicts stability up to about 2 years.

III. Water in Oil Mascara with Polyamide Gelling Agent

| Material | Weight % |
|---|---|
| Phase I | |
| Polyamide resin | 12.0 |
| PEG-30 Dipolyhydroxystearate | 3.0 |
| Cetyl acetate/Acetylated lanolin alcohol | 1.0 |
| Stearic acid | 3.0 |
| Isododecane | 20.0 |
| Phase II | |
| Black iron oxide | 10.0 |
| Ethanol | 3.0 |
| Glyceryl olivate | 0.5 |
| Isododecane | 18.0 |
| Phase III | |
| Acrylic copolymer | 7.0 |
| Dioctyl malate | 1.0 |
| Phase IV | |
| Water | 21.5 |

Add ingredients of Phase I together and heat to about 99° C. for about 2 hours. Combine Phase II ingredients and grind them in a Silverson at about 3000 rpm for about 10 minutes. Mix Phases I and II together, and add Phase III ingredients with a mixer at a temperature of about 80° C. Add phase IV ingredients to Phases I, II and III ingredients at about 80° C. by mixing and adjust pH to about 7.35.

IV. Comparative Study

A mascara composition containing polyamide as the emulsion gelling agent, substantially as described in Example II, is prepared and tested. A study is conducted in cool and warm climates for a period of 27 days. In the cool climate, 32 panelists are selected and are women ages 18 to 65 years old. The panelists wear conventional mascara at least 5 days per week and desire a mascara product that applies smoothly and feels comfortable. The panelists are instructed to use either the mascara of the present invention or a leading brand of mascara at least once a day. They are permitted to apply the mascara as often as they deem it to be necessary and/or desirable. However, they are to apply the mascara as they would apply their normal mascara. To remove the mascara the panelists are to use any normal eye makeup remover that they would ordinarily use.

At the conclusion of the study, panelists complete a self-administered questionnaire. Results of the study indicate that panelists who used the mascara of the present invention like it much more than the brand of mascara they normally use by 3 times more panelists who use the leading brand of mascara in the category of not clumping on the brush, separating the lashes, and curling the lashes. With respect to comfort on the lashes, defining the lashes, and the amount of color deposited to the lashes, 4 times as many panelists who use the mascara of the present invention like it much more than the mascara they normally use than panelists who use the leading brand of mascara. Finally, from the results of the study, 5 times as many panelists who use the mascara of the present invention than panelists who use the leading brand of mascara also indicate that the final appearance of lashes after application is liked much more than the mascara they normally use. Therefore, this study demonstrates the ability of incorporating the polyamide as a gelling agent for an emulsion in a mascara composition and the beneficial results obtained therefrom. The mascara of the present invention is non-tacky, therefore, it does not clump on the brush, and is comfortable when applied. Further, after the mascara of the present invention dries, the lashes appear nicely separated and defined, and have an overall appealing look that is preferred more than the leading brand of mascara.

What we claim is:

1. A lipstick or mascara composition comprising an emulsion of an aqueous phase and a non-aqueous phase, at least one inorganic pigment present in an amount greater than 2 percent by weight of the composition, and a gelling system of from about 0.01 to about 10 percent of at least one alkylene oxide-containing emulsion stabilizer having an HLB greater than 8, the alkylene oxide-containing emulsion stabilizer being selected from the group consisting of cetyl dimethicone copolyol/polyglycetyl-4 isostearate/hexyl laurate, PEG-30 dipolyhydroxystearate, sorbitan tristearate, glyceryl stearate/PEG-100 stearate, glyceryl olivate, polysorbate 20, stearic acid and laureth-7, and from about 1 to about 90 percent of at least one non-siloxane based polyamide resin, wherein the composition is wax-free and the non-siloxane based polyamide resin an ester-terminated polyamide of the following formula

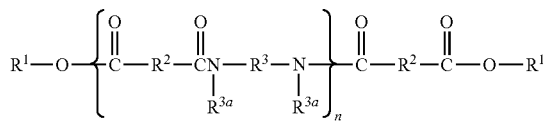

wherein:
each $R^1$ is independently alkyl or alkenyl;
each $R^2$ is independently a $C_{4-42}$ hydrocarbon, with the proviso that at least 50% of the R2 groups have 30-42 carbon atoms;
each $R^3$ is independently an organic group having at least two carbon atoms, optionally containing one or more oxygen or nitrogen atoms;
each $R^{3a}$ is independently hydrogen, $C_{1-10}$ alkyl, or a direct bond to $R^3$ or another $R^{3a}$ such that the N atom to which $R^3$ and $R^{3a}$ are both bonded is part of a heterocyclic structure defined in part by $R^{3a}$—N—$R^3$; and
n is the number of repeating units, such that ester groups constitute from 10% to 50% of the total of the ester and amide groups in the polyamide.

2. The composition of claim 1 wherein the at least one inorganic pigment is present in an amount greater than 5.0 percent by weight of the composition.

3. The composition of claim 1 wherein said non-aqueous phase further comprises volatile oil.

4. The composition of claim 1 further comprising an alkanolamide of a fatty acid.

5. The composition of claim 1 further comprising one or more active ingredients.

* * * * *